United States Patent [19]

Fruitstone et al.

[11] 4,259,207
[45] Mar. 31, 1981

[54] SUSPENDING MEDIUM FOR IMMUNOLOGIC REACTIONS

[75] Inventors: Mitchell J. Fruitstone; Michele M. Tilly; Betty G. Pixton, all of Miami, Fla.

[73] Assignee: American Hospital Supply Corporation, Evanston, Ill.

[21] Appl. No.: 76,716

[22] Filed: Sep. 19, 1979

[51] Int. Cl.³ ............... G01N 31/02; G01N 33/16; C09K 3/00
[52] U.S. Cl. ............... 252/408; 23/230 B; 424/11; 424/12; 424/359; 424/360; 424/89; 435/4; 435/5; 435/7
[58] Field of Search ............... 252/408; 424/12, 11, 424/88, 89, 101, 95, 360, 359; 23/230 B; 435/5, 7, 4

[56] References Cited

U.S. PATENT DOCUMENTS

| | | | |
|---|---|---|---|
| 3,565,987 | 2/1971 | Schuurs et al. | 424/12 |
| 3,970,427 | 7/1976 | Esposito et al. | 252/408 |
| 3,987,159 | 10/1976 | Spoma et al. | 424/12 |
| 4,003,988 | 1/1977 | Hoff et al. | 424/12 |
| 4,081,525 | 3/1978 | Knight et al. | 424/12 |
| 4,088,746 | 5/1978 | Blakemore et al. | 424/12 |
| 4,102,810 | 7/1978 | Armstrong | 252/408 |
| 4,139,606 | 2/1979 | Zichis | 23/230 B |
| 4,140,754 | 2/1979 | Iwasa | 424/12 |
| 4,170,454 | 10/1979 | Meriadec et al. | 252/408 |
| 4,202,872 | 5/1980 | Collen | 424/12 |

OTHER PUBLICATIONS

Atchley, W. A., et al., J. Immunology, vol. 93, pp. 701–712 (1964).
Wicker, B., et al., Transfusion, vol. 16, pp. 469–472 (1976).
Moore, H. C., et al., Transfusion, vol. 16, No. 4, pp. 291–296 (1976).
Garratty, G., et al., Clinical Res., vol. 26, p. 347A, (1978).
Hughes-Jones, N. C., et al. Vox Sang., vol. 9, pp. 385–395 (1964).
Hughes-Jones, N. C. et al., Immunology, vol. 7, pp. 72–81 (1964).
Elliot, M., et al., Vox Sang., vol. 9, pp. 396–414 (1964).
Fisk, R. T. et al., J. Clin. Path., vol. 17, pp. 737–740 (1947).
Rock, G., et al., Transfusion, vol. 18, No. 2, pp. 228–232 (1978).
Fitzsimmons, J. M., et al., Transfusion, vol. 19, No. 1, pp. 81–85 (1979).
Herron, R., et al., J. Clin. Path., vol. 31, pp. 1116–1117 (Nov. 1978).
Lincoln, P. J., et al. Vox Sang., vol. 34, pp. 221–226 (1978).
Issitt, P. D. et al., Advances in Immunohematology, vol. 6, No. 1 (prepared Mar. 1978).
"Technical Manual of The American Association of Blood Banks", 7th Ed., W. V. Miller, Ed., Am. Assn. of Blood Banks, Wash. D.C. p. 167 (1977).
Low, B., et al., Vox Sang., vol. 26, pp. 53–61 (1974).

*Primary Examiner*—Teddy S. Gron
*Attorney, Agent, or Firm*—Robert E. Hartenberger; Edward A. Figg

[57] ABSTRACT

A low ionic strength suspending medium for immunologic reactions which includes a salt solution, a buffer, gelatin, albumin, and an organic solute to control osmolality.

23 Claims, No Drawings

4,259,207

SUSPENDING MEDIUM FOR IMMUNOLOGIC REACTIONS

BACKGROUND OF THE INVENTION

The present invention relates to a suspending medium for use in immunologic reactions. More particularly, the invention relates to a suspending medium for immunohematologic reactions and to a method for potentiating agglutination reactions.

Immunohematologic agglutination reactions have conventionally been conducted in media comprised of physiological saline (ca.O.15M Na Cl) or albumin solutions. Thus, in antibody screening, antibody identification, crossmatches, direct or indirect antiglobulin testing, blood grouping, and the like, cells are conventionally washed and suspended in physiological saline for reaction with test serums. The use of physiological saline in such reactions suffers from certain disadvantages. Notably, lengthy incubation times are often required to observe agglutination reactions. In certain situations, such as crossmatching for emergency transfusions, it is important to obtain reaction results as quickly as possible. Another disadvantage of physiological saline is that cells tend to be sticky and, thus, adhere to glass surfaces, making evaluation of reaction results difficult.

Physiological saline has been modified to overcome some of these disadvantages. Esposito, V.M. and Weinstein, S.B., U.S. Pat. No. 3,970,427, describe a suspending solution containing physiological saline and a small amount of gelatin. The addition of gelatin was found to reduce or eliminate the problem of sticking between erythrocytes and glass surfaces, and to reduce hemolysis. Another procedure in widespread use involves the addition of an albumin solution, e.g. 22% or 30% bovine albumin, to a suspension of cells in physiological saline. The albumin is thought to enhance the agglutination reaction by reducing the electrostatic charge on the cell surfaces. *Technical Manual of the American Association of Blood Banks*, Wm. V. Miller, Ed., American Association of Blood Banks, Washington, D.C. 1977, p. 167.

For many years, low ionic strength solutions, i.e. solutions having ionic strengths lower than that of physiological saline, have been known to enhance agglutination in many immunologic tests. However, the procedures employing such solutions produced an unacceptable incidence of false (non-antibody) positive reactions and stymied their general acceptance. Low, B. and Messeter, L., *Vox. Sang.* 26, 53-61 (1974) reported a low ionic strength solution which included sodium glycinate. That solution produced few false positive reactions, and when compared to standard procedures employing physiological saline or bovine albumin, a reduction in required incubation times with specific antibody-containing serums was realized. The solution also increased the antibody uptake and the strengths of agglutination reactions with certain antibodies. Subsequent work indicates that procedures employing low ionic strength suspending media are at least as sensitive, and in most cases are more sensitive, than routine procedures employing physiological saline or albumin for the detection of IgG and IgM antibodies.

SUMMARY OF THE INVENTION

An object of the present invention is to provide an improved low ionic strength solution for use in immunologic reactions. A further object of the invention is to provide a low ionic strength suspending medium which enhances immunohematologic agglutination reactions.

In accordance with the invention, disclosed is an aqueous suspending medium for immunologic reactions, comprising gelatin, at a concentration of from about 0.5 wt. % to about 1.5 wt. %; albumin, at a concentration of from about 4.0 wt. % to about 6.0 wt. %; sufficient organic solute to provide an osmolality of from about 150 mOsm/kg. $H_2O$ to about 450 mOsm/kg. $H_2O$; sufficient sodium chloride, potassium chloride, or a mixture thereof to provide an ionic strength equivalent to about a 0.01 molar to about a 0.10 molar solution of sodium chloride; and a pH from about 6.0 to about 8.0.

DETAILED DESCRIPTION OF THE INVENTION

The suspending medium of the present invention has a low ionic strength, as compared to physiological saline. Sodium or potassium chloride or a mixture thereof is usually added to the solution to provide the desired ionic strength, but ions from other sources, such as buffers, pH adjusting agents, and albumin, also contribute to the ionic strength of the final product. Therefore, to determine the quantity of sodium or potassium chloride to be added, the electrical conductivity (or resistivity) of the solution may be used as a measure of ionic strength. The absolute value of the electrical conductivity is not critical, but the measurement is useful for comparison to solutions of known ionic strengths. The ionic strength of the suspending medium of the present invention is equivalent to about a 0.01 molar to about 0.1 molar aqueous sodium chloride solution. Preferably, the ionic strength will be equivalent to about a 0.02 molar to about 0.05 molar sodium chloride solution. It is not necessary to measure the electrical conductivity of each batch of solution, once the desired formula is determined, but the measurement is useful for initially determining the relative proportions of ingredients for a specific formulation.

The solution includes gelatin at a concentration of from about 0.5 wt. % to about 1.5 wt. %, preferably from about 0.7 wt. % to about 1.3 wt. %. The gelatin used in this invention is advantageously finely divided to facilitate dissolution, and is preferably of at least laboratory grade purity in accordance with the listing in the U.S. Pharmacopea or National Formulary.

The source of the gelatin and the procedures used in its preparation are not critical. Thus, gelatin obtained from the partial hydrolysis of collagen derived from calfskin, pigskin, and the skin, white connective tissue, and bones of various animals all appear suitable. Similarly, the gelatin may be derived from an acid-treated precursor (Type A) or from an alkali-treated precursor (Type B).

Albumin is also advantageously dissolved in the solution at a concentration of from about 3.0 wt. % to about 7.0 wt. %, preferably from about 4.0 wt. % to about 6.0 wt. %. The source of the albumin used is not critical. Bovine serum albumin is preferable because of its availability and cost, but albumin obtained from the fractionation of plasma from virtually any animal, such as horse, sheep, swine, chicken and human, may be employed. The albumin is preferably substantially salt-free or low in salt, so as not to contribute appreciably to the ionic strength of the final solution. The effect of the salt concentration of the albumin on ionic strength should be considered when determining the concentration of other ingredients.

Because the ionic strength of the solution of the present invention is lower than that of physiological saline, the osmolality must be adjusted to approximate physiological values. If the osmolality of the solution is too low, the erythrocytes will lyse, and if it is too high, they will become crenated. The osmolality of the present solutions is controlled within a range of from about 150 mOsm/kg. $H_2O$ to about 450 mOsm/kg. $H_2O$. Preferably, the osmolality is adjusted from about 250 mOsm/kg. $H_2O$ to about 400 mOsm/kg. $H_2O$. Any solute which does not substantially increase the ionic strength of the solution, and which does not deleteriously react with any other components of the solution or interfere with the immunologic reaction may be employed to control osmolality. Such solute is preferably organic, such as an amino acid, a sugar, a soluble alcohol, etc. Particularly preferred solutes are glycine, sucrose, and glucose.

The optimum pH for immunologic reactions varies from one antibody or antibody group to another. For a universal suspending medium, the pH is advantageously adjusted to provide near optimum conditions for the greatest number of tests. Accordingly, the pH of the suspending media of this invention is adjusted from about 6.0 to about 8.0. A preferred pH range is from about 6.4 to about 7.4. The pH may be adjusted with an acid or a base as is well known in the art. Mineral acids such as hydrochloric acid, sulfuric acid, and the like and alkali or alkaline earth metal hydroxides such as sodium hydroxide, potassium hydroxide, etc. are used. To provide greater control of pH, a suitable buffer may be used in a pH-controlling amount. Any buffer capable of controlling pH within the desired range and which does not interfere with the reaction, may be employed. Conventional phosphate buffers are preferred for this purpose.

The ingredients of the suspending medium may be combined in any convenient manner. A preferred manner of preparing the solution is to sequentially dissolve the ingredients in a portion of the total volume of water to be used. The water may be heated, e.g. to 50° C.–60° C. and stirred to facilitate dissolution of the gelatin. After the gelatin is dissolved, the remaining ingredients are dissolved in the solution. The pH is then adjusted and the remaining water is added.

The solution will usually be packaged and stored for extended periods of time; therefore, it is desirable to sterilize the solution and to incorporate a preservative therein. Sterilization may be accomplished by any convenient means such as sterile filtration, irradiation, and the like. Suitable preservatives include conventional bacteriostats or antibiotics such as preserving amounts of thimerosal, phenylmercuric acetate, sodium azide, neomycin or chloramphenicol, or combinations thereof.

The solutions of this invention may be employed in a wide variety of immunologic reactions. They are particularly useful in immunohematologic reactions, such as antibody screening, antibody identification, crossmatches, direct or indirect antiglobulin testing, blood grouping, and the like. The solutions may also be used in other types of immunologic reactions, such as latex particle agglutination tests, e.g., as in the latex agglutination assay for hepatitis surface antigen, and other antibody/antigen reactions.

The present invention constitutes a significant advance over previous suspending media for hematologic reactions. The addition of gelatin to a low ionic strength solution was found to improve the performance of that solution. Agglutination reactions were stronger and more easily interpreted, and incubation times were reduced.

Surprisingly, the incorporation of both albumin and gelatin into the formulation resulted in a suspending medium having properties much improved over conventional albumin or saline solutions, or glycine-containing low ionic strength solutions. Sensitivity was greater than that of the solution containing only gelatin, resuspension was facilitated, and there were fewer questionable or rough looking negative reactions. Moreover, the incidence of nonspecific agglutination reactions or false positives has been found to be quite low with these solutions.

In addition to its use in antibody detection, antibody identification, and compatibility testing, the suspending medium of the present invention may be utilized as the base for preparation of various blood grouping serums. These serums have the advantages of increased sensitivity and decreased reaction times that are found using low ionic strength solutions with patient antibodies. The increased sensitivity allows less antiserum (or lower titers) to be used for preparation of blood grouping serums of at least equal reactivity to conventional serums. The cost savings associated with such serums is apparent.

Thus, a new low ionic strength solution has been discovered which possesses antibody-enhancing characteristics superior to the solutions currently used in blood banking. Increased sensitivity is realized while the incubation times required for both IgG and IgM antibodies are reduced.

The invention is further illustrated by the following examples which are not intended to be limiting.

EXAMPLE I

Approximately 400 kg. of purified water was charged into a stainless steel tank equipped with an agitator and a heating means. The water was heated to 50° C.–60° C. Gelatin (8.0 kg.) was added to the water and the mixture was stirred for 2–2½ hours at 50° C.–60° C. The temperature was maintained while albumin (343 kg. of 15% solution), sodium chloride (716 g), glycine (21.6 kg.), sodium phosphate dibasic (85 g), sodium phosphate monobasic (83 g), and thimerosal (100 g) were dissolved. The pH of the solution was adjusted to 6.9±0.1 with 1N sodium hydroxide, and water was added to a final weight of 1019 kg. The solution was sterile filtered while hot and filled into bottles.

EXAMPLE II

The suspending medium described in Example I was tested by blood bank laboratories in over 1700 assays involving identification of representative samples of all major blood groups. The tests were designed to confirm the efficacy of the solution and compare it to standard procedures employed by blood banks. Cells and serums were obtained from patient samples routinely submitted to the laboratory. No selection of patient population by age, sex, medication, disease state, etc. was made. The basic testing performed on patient samples included an autocontrol consisting of the patients' cells with autologous serum, a direct antiglobulin test on patients' cells and an antibody screen on the patients' serum. If the antibody screen was positive, an antibody identification panel was employed to attempt to identify the specificity of the antibody.

Assays were conducted by adding to a test tube 2 drops of patient serum, 1 drop of a 3%–5% saline cell suspension, and 4 drops of the suspending medium. Where sufficient patient sample was available, two tubes were prepared for each sample. One tube was centrifuged immediately, examined immediately after centrifugation, after 10 minutes at room temperature, and again after 5 minutes at 5° C. The second tube was examined after 15 minutes at 37° C. and again after washing and addition of anti-human (Coombs) serum. When insufficient sample was available for two tube testing, one tube was used. The tube was examined immediately after centrifugation, after room temperature incubation (10 minutes), after incubation at 37° C. for 15 minutes, and again after washing and addition of the anti-human serum.

Parallel samples were assayed by standard methods conventionally employed in the laboratory. These involved either a saline method, employing physiological saline or a "high protein" method, employing 22% or 30% albumin. In the saline procedure each tube received 2 drops of patient serum and 1 drop of 3%–5% saline cell suspension. In the high protein procedure, each tube received 2 drops of patient serum, 3 drops of albumin solution, and 1 drop of 3%–5% saline cell suspension.

Reactions were observed using some type of optical aid such as an agglutination viewer. The reactions were read macroscopically and graded as follows:

4+ = One large cell button that remains intact on gentle resuspension.

3+ = Several large agglutinates of cells on gentle resuspension.

2+ = Many small agglutinates of approximately equal size, clear background.

1+ = Many small but definite agglutinates, finely granular appearance, opaque reddish background.

± = Minute agglutinates, many unagglutinated cells.

h = Hemolysis.

— = Negative reaction. No agglutination.

Interpretation:

Positive-Cells agglutinated

Negative-No agglutination.

Intermediate gradations using superscript "s" for stronger and "w" for weaker were used; e.g., $1^s, 1^w$, etc., creating a total of twelve agglutination strengths (12 point scale).

The results of the tests were reported and grouped according to each antibody. The data was summarized and comparisons to standard tests were made. The performance of the suspending medium of the present invention as compared to standard procedures are listed in Table I. The first column of Table I indicates the particular antibody/antigen reaction observed, column 2 indicates the point at which an observation was made: LT = after five minutes incubation at 5° C., RT = after 10 minutes incubation at room temperature, 37 = after 15 minutes incubation at 37° C., AG = after cell washing and addition of anti-human serum. Columns 3 and 4 indicate the performance of the solution of present invention to standard procedures for antibody screen results and panel results. In the subcolumn under >Std., the percentage of expected positive reactions which were significantly stronger than the standard procedure (i.e. having a reaction strength separated by at least a 1+ difference) are listed. Likewise, the subcolumn under = Std. lists the percentage of expected positive reactions for the test medium equivalent to the standard procedure (i.e. separated by less than 1 + difference), and the subcolumn under <Std., lists the percentage of expected positive reactions for the test medium significantly weaker than the standard procedure (separated by greater than 1 + difference). Note that a positive test is always considered significant over negative test even if the reaction strengths differ by less than 1 +. A positive reaction is defined as any reaction having a strength of ± or greater.

Although the performance of the suspending medium of this invention varied from one antibody to another, overall, the solution performed significantly better than standard procedures. Each antibody/antigen group was assayed at all four phases for evaluation purposes. Under normal testing conditions, those skilled in the art recognize that certain phases are more reliable for antibodies having certain blood group specificities. In Table I, the phases conventionally used for particular antibodies are indicated by asterisks.

EXAMPLE III

In this example, a procedure employing the suspending medium described in Example I was compared to procedures employing low ionic strength saline plus glycine, low ionic strength saline plus albumin, and standard procedures as described in Example II.

Serums were selected based on prior data indicating the presence of specific antibodies, without regard to patient sex, age, disease status, etc. Red cells were commercial reagent screening cells having known antigenic compositions. Reactions were rated on a twelve point system as described in Example II except that reaction strengths were expressed on a linear scale from negative (0) to 12(4+).

The experimental results are reported in Table II. Solution A is the suspending medium described in Example I. Solution B is a commercial phosphate buffered low ionic strength saline solution containing glycine and a preservative. Solution C is a commercial phosphate buffered low ionic strength saline solution containing 5% albumin. The Standard Method involves initial reaction in physiological saline, followed by addition of 3 drops of 30% albumin for the 37° C.incubation, then conversion to antiglobulin (Coombs) testing.

All assays were one tube tests. Procedures using the suspending medium described in Example I were conducted as described in Example II. In procedures using Solution B, cells were washed with physiological saline and a 3% cell suspension in Solution B was prepared. Two drops of serum was added to one drop of the cell suspension. The cells were centrifuged and observed after 10 minutes incubation at room temperature, resuspended and reexamined after incubation at 37° C. for 15 minutes, and then converted to antiglobulin (Coombs) testing. In procedures using Solution C, two drops of serum were mixed with one drop of a 3-5% suspension of cells in physiological saline and four drops of Solution C were added. The reactions were examined in the same manner as with Solution B.

The reaction scores listed in Table II indicate that the suspending medium of the present invention results in greater sensitivity than the other media, and the test totals demonstrate an overall superiority.

TABLE I

| Anti-body | Phase | Antibody Screen Results | | | Panel Results | | |
|---|---|---|---|---|---|---|---|
| | | >Std | =Std | <Std | >Std | =Std | <Std |
| D | LT | | | | | | |
| | RT | 7 | 7 | 7 | 0 | 0 | 8 |
| | 37 | 0 | 0 | 29 | 5 | 0 | 26 |
| | AG* | 50 | 43 | 0 | 43 | 52 | 4 |
| C | LT | | | | | | |
| | RT | | | | | | |

TABLE I-continued

| Anti-body | Phase | Antibody Screen Results | | | Panel Results | | |
|---|---|---|---|---|---|---|---|
| | | >Std | =Std | <Std | >Std | =Std | <Std |
| $Fy^a$ | LT | | | | | | |
| | RT | | | | | | |
| | 37 | | | | | | |
| | AG* | | | | 35 | 65 | 0 |

TABLE II

| TEST PHASE→ | 10 minutes Room Temperature | | | | 15 minutes 37° C. | | | | Antiglobulin Serum | | | |
|---|---|---|---|---|---|---|---|---|---|---|---|---|
| TEST METHOD→ | Sol'n. A | Sol'n. B | Sol'n. C | Standard Method | Sol'n. A | Sol'n. B | Sol'n. C | Standard Method | Sol'n. A | Sol'n. B | Sol'n. C | Standard Method |
| Antibody | | | | | | | | | | | | |
| Anti-D | 10 | 3 | 6 | 0 | 9 | 3 | 6 | 6 | 10 | 11 | 10 | 8 |
| Anti-D | 0 | 0 | 0 | 0 | 0 | 0 | 0 | 0 | 9 | 6 | 9 | 3 |
| Anti-D + C | 0 | 0 | 0 | 0 | 3 | 0 | 0 | 0 | 11 | 10 | 11 | 9 |
| Anti-E | 0 | 0 | 0 | 0 | 3 | 0 | 1 | 1 | 0 | 1 | 0 | 0 |
| Anti-e | 3 | 0 | 4 | 0 | 0 | 0 | 0 | 3 | 3 | 0 | 3 | 3 |
| Anti-M | 10 | 5 | 12 | 0 | 9 | 1 | 9 | 1 | 8 | 0 | 4 | 3 |
| Anti-S | 6 | 0 | 3 | 0 | 3 | 0 | 0 | 0 | 3 | 0 | 3 | 2 |
| Anti-$P_1$ | 6 | 3 | 5 | 3 | 5 | 3 | 0 | 0 | 3 | 1 | 1 | 3 |
| Anti-$Le^a$ | 10 | 9 | 9 | 7 | 6 | 3 | 4 | 3 | 1 | 3 | 0 | 3 |
| Anti-$Le^{bH}$ | 6 | 4 | 0 | 0 | 0 | 0 | 0 | 0 | 0 | 0 | 0 | 0 |
| Anti-K | 3 | 0 | 0 | 0 | 3 | 0 | 0 | 0 | 11 | 9 | 11 | 12 |
| Anti-$Fy^a$ | 3 | 4 | 3 | 0 | 4 | 3 | 7 | 0 | 5 | 5 | 3 | 6 |
| Anti-$Jk^a$ | 0 | 0 | 0 | 0 | 0 | 0 | 0 | 0 | 9 | 11 | 9 | 3 |
| Total Score | 47 | 28 | 42 | 10 | 45 | 10 | 27 | 14 | 73 | 57 | 64 | 55 |

| | | | | | | | |
|---|---|---|---|---|---|---|---|
| | 37 | | | | | | |
| | AG* | | | | 60 | 0 | 0 |
| $\overline{c}$ | LT | | | | | | |
| | RT | | | | 3 | 22 | 0 |
| | 37 | | | | 3 | 22 | 0 |
| | AG* | 50 | 50 | 0 | 19 | 63 | 3 |
| E | LT | 33 | 0 | 0 | 15 | 7 | 0 |
| | RT | 38 | 0 | 0 | 69 | 6 | 3 |
| | 37 | 13 | 25 | 13 | 13 | 26 | 3 |
| | AG* | 25 | 75 | 0 | 54 | 77 | 0 |
| $\overline{e}$ | LT | | | | | | |
| | RT | | | | | | |
| | 37 | | | | 0 | 0 | 45 |
| | AG* | | | | 0 | 90 | 10 |
| M | LT | 0 | 0 | 0 | 3 | 39 | 0 |
| | RT* | 75 | 25 | 0 | 66 | 10 | 3 |
| | 37 | 25 | 0 | 0 | 50 | 6 | 1 |
| | AG | 0 | 25 | 25 | 22 | 37 | 3 |
| N | LT | | | | 30 | 0 | 0 |
| | RT* | | | | 33 | 48 | 15 |
| | AG | | | | | | |
| S | LT | | | | | 80 | 20 |
| | RT* | | | | | 100 | |
| | 37 | | | | | 100 | |
| | AG | | | | | 100 | |
| $P_1$ | LT | 0 | 25 | 0 | 20 | 74 | 6 |
| | RT* | 25 | 75 | 0 | 22 | 52 | 7 |
| | 37 | 25 | 0 | 75 | 0 | 26 | 7 |
| | AG* | 0 | 25 | 50 | 9 | 37 | 11 |
| $Le^a$ | LT | | | | | | |
| | RT* | 8 | 42 | 25 | 6 | 39 | 19 |
| | 37 | 8 | 17 | 50 | 7 | 65 | 31 |
| | AG* | 13 | 33 | 50 | 9 | 40 | 24 |
| $Le^b$ | LT | | | | | | |
| | RT | 17 | 22 | 6 | 16 | 41 | 22 |
| | 37 | 11 | 11 | 22 | 12 | 27 | 25 |
| | AG* | 6 | 17 | 17 | 13 | 35 | 21 |
| K | LT | 0 | 0 | 17 | 30 | 10 | 0 |
| | RT | 8 | 33 | 8 | 6 | 36 | 3 |
| | 37 | 8 | 33 | 0 | 6 | 25 | 0 |
| | AG* | 33 | 67 | 0 | 17 | 78 | 3 |
| $\overline{k}$ | LT | | | | | | |
| | RT | | | | | | |
| | 37 | | | | | | |
| | AG* | | | | 80 | 20 | 0 |
| $Kp^a$ | LT | | | | | | |
| | RT | | | | | | |
| | 37 | | | | | | |
| | AG* | | | | 0 | 67 | 33 |

We claim:

1. A suspending medium for an immunologic reaction, comprising gelatin, at a concentration of from about 0.5 wt. % to about 1.5 wt. %; albumin, at a concentration of from about 4.0 wt. % to about 6.0 wt. %; sufficient organic solute to provide an osmolality of from about 150 mOsm/kg. $H_2O$ to about 450 mOsm/kg. $H_2O$; sufficient sodium chloride, potassium chloride, or a mixture thereof to provide an ionic strength equivalent to about a 0.01 molar to about a 0.10 molar solution of sodium chloride; and a pH from about 6.0 to about 8.0.

2. The suspending medium of claim 1 wherein the gelatin concentration is from about 0.7 wt. % to about 1.3 wt. %.

3. The suspending medium of claim 1 wherein the gelatin concentration is from about 0.7 wt. % to about 1.3 wt. % and the albumin concentration is from about 4.0 wt.% to about 6.0 wt.%.

4. The suspending medium of claim 3 wherein the albumin is substantially salt-free bovine serum albumin.

5. The suspending medium of claim 1 wherein the osmolality is from about 250 mOsm/kg. $H_2O$ to about 400 mOsm/kg. $H_2O$.

6. The suspending medium of claim 3 wherein the osmolality is from about 250 mOsm/kg. $H_2O$ to about 400 mOsm/kg. $H_2O$.

7. The suspending medium of claim 6 wherein the organic solute is an amino acid, a sugar, or a water soluble alcohol.

8. The suspending medium of claim 6 wherein the organic solute is glycine, sucrose, or glucose.

9. The suspending medium of claim 6 wherein the organic solute is glycine.

10. The suspending medium of claim 1 wherein the pH is from about 6.4 to about 7.4.

11. The suspending medium of claim 3 wherein the pH is from about 6.4 to about 7.4.

12. The suspending medium of claim 8 wherein the pH is from about 6.4 to about 7.4.

13. The suspending medium of claim 1, further comprising a pH-controlling amount of a buffer.

14. The suspending medium of claim 13 wherein the buffer is a phosphate buffer.

15. The suspending medium of claim 3, further comprising a pH-controlling amount of a phosphate buffer.

16. The suspending medium of claim 8, further comprising a pH-controlling amount of a phosphate buffer.

17. The suspending medium of claim 1, further comprising a preserving amount of a bacteriostat or an antibiotic.

18. The suspending medium of claim 17, wherein the antibiotic is neomycin or chloramphenicol, or the bacteriostat is thimerosal, phenylmercuric acetate, or sodium azide.

19. The suspending medium of claim 3, further comprising a preserving amount of thimerosal.

20. The suspending medium of claim 8, further comprising a preserving amount of thimerosal.

21. The suspending medium of claim 16, further comprising a preserving amount of thimerosal.

22. The suspending medium of claim 1, 3, 4, 8, 9, 12, 16, or 20, wherein the ionic strength is equivalent to about a 0.02 molar to about 0.05 molar sodium chloride solution.

23. The suspending medium of claim 22 wherein the immunologic reaction is an immunohematologic reaction.

* * * * *